US00PP29772P2

(12) United States Plant Patent
Smith

(10) Patent No.: US PP29,772 P2
(45) Date of Patent: Oct. 23, 2018

(54) ***CHRYSANTHEMUM* PLANT NAMED 'CIFZ0056'**

(50) Latin Name: ***Chrysanthemum* x *morifolium***
Varietal Denomination: CIFZ0056

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,489

(22) Filed: Jan. 19, 2017

(51) Int. Cl.
*A01H 5/02* (2018.01)

(52) U.S. Cl.
USPC ..... Plt./287

(58) Field of Classification Search
USPC ..... Plt./287, 292, 291
CPC ..... A01H 5/0255; A01H 5/00; A01H 5/025; A01H 5/02; A01H 6/14
See application file for complete search history.

*Primary Examiner* — June Hwu
(74) *Attorney, Agent, or Firm* — Dale Skalla

(57) ABSTRACT

A new garden type *Chrysanthemum* plant named 'CIFZ0056' particularly distinguished by the small size pink/lavender decorative flower, large size plant with round sphere plant habit and a natural season response in mid-late October.

1 Drawing Sheet

Latin name of the genus and species of the plant claimed: *Chrysanthemum* x *morifolium.*

Varietal denomination: 'CIFZ0056'.

BACKGROUND OF THE NEW PLANT

The present invention comprises a new *Chrysanthemum*, botanically known as *Chrysanthemum* x *morifolium*, and hereinafter referred to by the variety name 'CIFZ0056'.

'CIFZ0056' is a product of a planned breeding program. The new cultivar has small size pink/lavender decorative flower, large size plant with round sphere plant habit and a natural season response in mid-late October.

'CIFZ0056' originated from a mutation: Stock x-rayed at 1750 RAD in October of 2013. Single cutting sport from the stock.

The female parent was the unnamed lavender/pink colored seedling from own breeding '11-M262'.

When compared to the female parent, 'CIFZ0056 has:

1) Similar flower type and size but distinctly lighter lavender/pink color than the sport parent
2) Blackcloth and natural season response is similar or a day slower than the sport parent
3) Similar plant habit and slightly larger plant size than the sport parent No male parent.

The first act of asexual reproduction of 'CIFZ0056' was accomplished when vegetative stem tip cuttings were propagated from the initial selection, this initial selection took place on Apr. 16, 2014 in Gilroy, Calif.

BRIEF SUMMARY OF INVENTION

Horticultural examination of plants grown from cuttings of the plant initiated May 2014 in Gilroy, Calif., and continuing thereafter, has demonstrated that the combination of characteristics as herein disclosed for 'CIFZ0056' are firmly fixed and are retained through successive generations of asexual reproduction.

'CIFZ0056' has not been observed under all possible environmental conditions. The phenotype may vary significantly with variations in environment such as temperature, light intensity and day length.

'CIFZ0056' has not been made publicly available prior to the effective filing date of this application, notwithstanding any disclosure that may have been made less than one year prior to the effective filing date of this application by the inventor or another who obtained 'CIFZ0056' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

Figure 1:
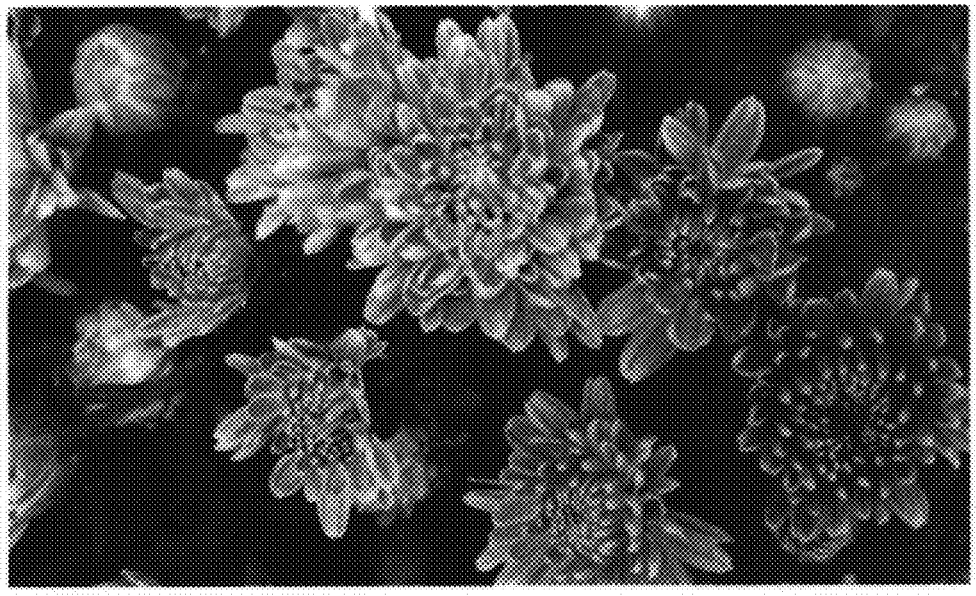
Figure 2:
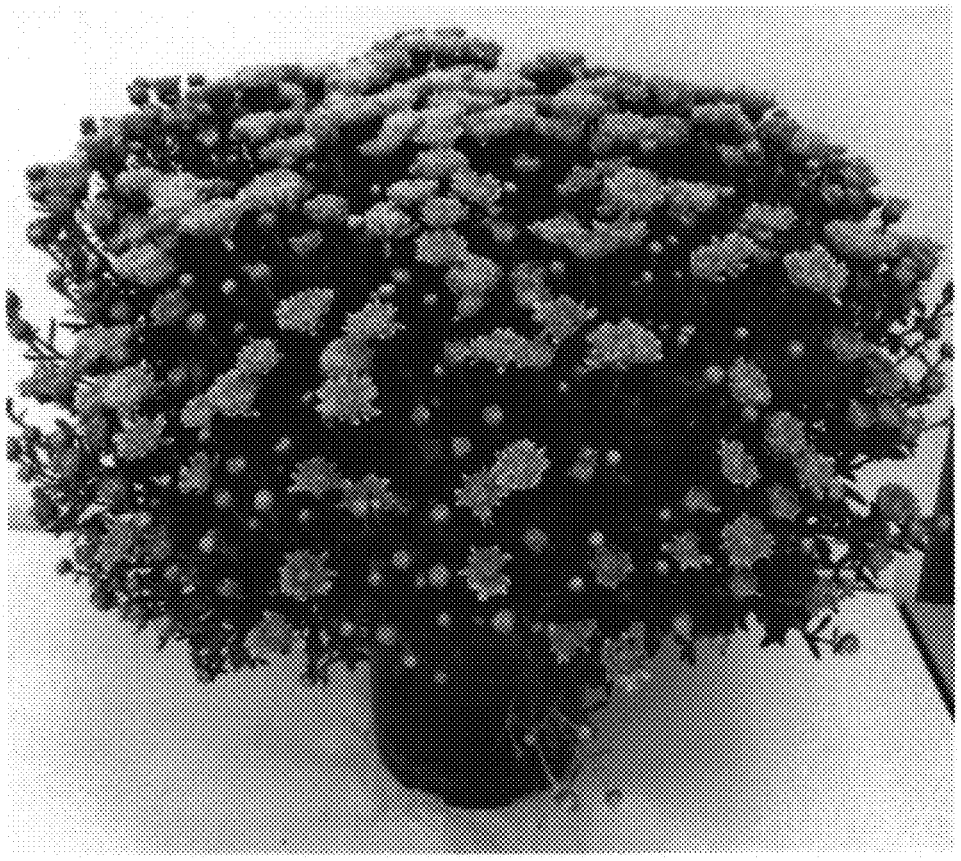

The accompanying photographic drawings show typical flower and foliage characteristics of 'CIFZ0056' with colors being as true as possible with an illustration of this type. The photographic drawings shown in FIG. 1 is a close-up view of the flowers of the new variety and in FIG. 2 is a flowering plant from an outdoor trial.

The aforementioned photographs: FIG. 1, as well as FIG. 2, were taken in October 2016 both showing a plant from the same natural outdoor trial in Gilroy, Calif. These plants were about 18 weeks of age. One rooted cutting per pot had been planted in a one gallon pot, not pinched in week 22. Plants started flowering end of September.

DETAILED BOTANICAL DESCRIPTION

The measurements were taken in Gilroy, Calif. in October, 2016 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0056' AND 'Yobarbie'

| | 'CIFZ0056' | 'Yobarbie', U.S. Plant Pat. No. 17,008 |
|---|---|---|
| Flowering response (blackcloth): | 1 week slower | 1 week faster |
| Flowering response (natural): | Similar | Similar |
| Flower color: | Bit lighter color | Bit darker color |
| Flower size: | Bit smaller flower | Bit bigger flower |
| Plant habit or size: | Larger plant with more spread and therefore rounder habit especially in blackcloth compared to 'Yobarbie' | Larger plant with more oval habit especially in blackcloth compared to 'CIFZ0056' |

TABLE 2

DIFFERENCES BETWEEN THE NEW VARIETY 'CIFZ0056' AND 'Staviski Dark Pink'

| | 'CIFZ0056' | 'Staviski Dark Pink', U.S. Plant Pat. No. 21,901 |
|---|---|---|
| Flowering response (blackcloth): | 1 week slower | 1 week faster |
| Flowering response (natural): | Similar | Similar |
| Frost tolerance: | Frost tolerant | Not frost tolerant |
| Flower shape: | Less disc florets | More disc florets |
| Plant habit or size: | Larger plant size | Smaller plant size |

Plant:

*Form, growth and habit.*—Herbaceous garden-type, stems upright and outwardly spreading, freely branching, strong and moderately vigorous growth habit.

*Plant height (above soil).*—21-26 cm.

*Plant height (inflorescence included).*—24-29 cm.

*Plant width.*—43-47 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 139A.

*Mature leaf, color lower surface.*—RHS 137B.

*Length.*—3.6-4.0 cm.

*Width.*—2.4-3.0 cm.

*Shape.*—Ovate.

*Base shape.*—Attenuate.

*Apex shape.*—Acute.

*Margin.*—3 main lobes, irregularly serrated.

*Texture, upper surface.*—Bifid hairs.

*Texture, lower surface.*—Bifid hairs.

*Color of veins, upper surface.*—RHS 139B.

*Color of veins, lower surface.*—RHS 139C.

*Pattern of veining.*—Palmate.

*Petiole color.*—RHS 138B.

*Petiole length.*—1.6-1.8 cm.

*Diameter.*—0.2 cm.

*Texture.*—Covered with bifid hairs.

Stem:

*Quantity of main branches per plant.*—12-14.

*Color of stem.*—RHS 138B.

*Length of stem.*—12-14 cm.

*Diameter.*—0.3-0.5 cm.

*Length of internodes.*—0.8-2.2 cm.

*Texture.*—Bifid hairs.

*Color of peduncle.*—RHS 138B.

*Length of peduncle.*—5.6-6.1 cm.

*Peduncle diameter.*—0.15 cm.

*Texture.*—Bifid hairs.

Inflorescence:

*Type.*—Compositae, solitary, decorative-type inflorescences borne terminally above foliage, ray florets arranged on a capitulum.

*Quantity of short days to flowering (response time).*—Approximately 7 weeks.

*Natural season flowering.*—Mid-late October.

*Quantity of inflorescences per plant.*—210-250, with small buds developing.

*Lastingness of individual blooms on the plant.*—About six weeks from first color.

*Fragrance.*—Slightly spicy.

Bud (when showing color):

*Color.*—Closest to RHS 76A.

*Length.*—0.8-1.2 cm.

*Width.*—0.8-1.1 cm.

*Shape.*—Oblate.

Immature inflorescence:

*Diameter.*—1.4-2.2 cm.

*Color of ray florets, upper surface.*—RHS 78B with tips of RHS 155D.

*Color of ray florets, lower surface.*—RHS 78B, with tips of RHS 155D.

Mature inflorescence:

*Diameter.*—2.7-3.1 cm.

*Depth.*—1.7-1.9 cm.

*Total diameter of disc.*—Very small; not visible as covered by the many rays.

*Receptacle color.*—RHS 145A.

*Receptacle height.*—0.4 cm.

*Receptacle diameter.*—0.7-1.1 cm.

Ray florets:

*Average quantity of florets.*—Between 150 and 180 in many whorls.

*Color of florets, upper surface.*—RHS 77C with tips RHS 155D.

*Color inner surface.*—RHS 77C with tips RHS 155D.

*Length.*—0.9-1.0 cm.

*Width/diameter.*—0.3-0.4 cm.

*Shape.*—Oblong to elliptical.

*Apex shape.*—Most often emarginated or praemorse.

*Base shape.*—Attenuate.

*Margin.*—Entire.

*Texture, upper surface.*—Smooth.

*Lower surface.*—Smooth.

Disc florets:

*Average quantity of florets.*—32.

*Color of florets.*—RHS 1C.

*Length.*—0.2-0.3 cm.

*Width.*—0.1 cm.

*Shape.*—Tubular, elongated.

*Apex shape.*—Acute, 5 pointed.

Phyllaries:

*Quantity*.—Approximately 100.

*Color, upper surface*.—RHS 137A.

*Color, lower surface*.—RHS 137B.

*Length*.—0.6-0.7 cm.

*Width*.—0.15-2.0 cm.

*Shape*.—Lanceolate.

*Apex shape*.—Acute.

*Base*.—Fused.

*Margins*.—Entire, some with papery edges.

*Texture, upper surface*.—Glabrous.

*Texture, lower surface*.—Bifid hairs.

Reproductive organs:

*Pistil*.—One.

*Length*.—0.3-0.6 cm.

*Style color*.—RHS 1C.

*Style length*.—0.35-0.4 cm.

*Stigma color*.—RHS 7D.

*Stigma shape*.—Bi-parted.

*Ovary color*.—RHS 145D.

*Ovary length*.—0.15 cm.

*Ovary width*.—0.1 cm.

Androecium:

*Stamens*.—None, as they are usually present in disc florets only, which are not developed.

*Fertility/seed set*.—Has not been determined to date.

*Disease/pest resistance*.—Has not been determined to date.

*Cold tolerance*.—Frost tolerant.

What is claimed is:

1. A new and distinct variety of *Chrysanthemum* plant named 'CIFZ0056' substantially as illustrated and described herein.

* * * * *